(12) United States Patent
Sundermeyer et al.

(10) Patent No.: US 8,076,500 B2
(45) Date of Patent: Dec. 13, 2011

(54) PRODUCTION OF N-ARYL CARBAMATES AND N-ARYL ISOCYANATES

(75) Inventors: Joerg Sundermeyer, Marburg (DE); Fuming Mei, Wuhan (CN)

(73) Assignee: Philipps-Universitaet Marburg, Marburg (DE)

( * ) Notice: Subject to any disclaimer, the term of this patent is extended or adjusted under 35 U.S.C. 154(b) by 333 days.

(21) Appl. No.: 11/921,972

(22) PCT Filed: Jun. 9, 2006

(86) PCT No.: PCT/EP2006/005516
§ 371 (c)(1),
(2), (4) Date: Apr. 14, 2010

(87) PCT Pub. No.: WO2006/131381
PCT Pub. Date: Dec. 14, 2006

(65) Prior Publication Data
US 2010/0217029 A1 Aug. 26, 2010

(30) Foreign Application Priority Data
Jun. 9, 2005 (DE) .......................... 10 2005 026 500

(51) Int. Cl.
*C07C 261/00* (2006.01)
*C07C 269/00* (2006.01)
*C07C 271/00* (2006.01)

(52) U.S. Cl. ........................................ 560/24
(58) Field of Classification Search ................ None
See application file for complete search history.

(56) References Cited

U.S. PATENT DOCUMENTS

| 3,448,140 | A | * | 6/1969 | Ibbotson et al. | 560/24 |
| 3,481,967 | A | * | 12/1969 | Ottmann et al. | 560/342 |
| 4,705,883 | A | * | 11/1987 | Grate et al. | 560/25 |
| 2005/0124556 | A1 | * | 6/2005 | Burton | 514/23 |

OTHER PUBLICATIONS

Khan et al., Reductive Carbonylation of Nitrobenzene to Phenylurethane Catalyzed by Ru(III)-Schiff Base Complexes, J. Mol. Cat., 1990, 57(3), 301-305.*

* cited by examiner

*Primary Examiner* — Daniel Sullivan
*Assistant Examiner* — Jennifer C Sawyer
(74) *Attorney, Agent, or Firm* — Clark & Brody

(57) ABSTRACT

A method for the production of N-aryl carbamates (urethanes) and N-aryl isocyanates is described in which aromatic nitro compounds are subjected to a reductive carbonylation in the presence of carbon monoxide and organic compounds carrying hydroxyl groups, wherein the carbonylation is carried out in the presence of metal complex catalysts, for which anionic N,O chelate ligands of the general type $[M(N{\sim}O)^-_2]$ and $[M(O{\sim}N{\sim}N{\sim}O)^{2-}]$ containing a bi- or trivalent transition metal of the groups 5 to 11 are used.

9 Claims, No Drawings

PRODUCTION OF N-ARYL CARBAMATES AND N-ARYL ISOCYANATES

CROSS REFERENCE TO RELATED APPLICATIONS

This application is the US national phase of PCT application PCT/EP2006/005516, filed 9 Jun. 2006, published 14 Dec. 2006 as WO 2006/131381, and claiming the priority of German patent application 102005026500.6 itself filed 9 Jun. 2005, whose entire disclosures are herewith incorporated by reference.

The subject of the present invention is a method for producing N-aryl carbamates (urethanes) and/or N-aryl isocyanates through reductive carbonylation of aromatic nitro compounds in the presence of carbon monoxide and alcohols.

Aryl diisocyanates, for example toluene diisocyanate TDI, are technically important intermediates for the production of polyurethanes, which have, for example, numerous applications as foams. They are usually obtained from dinitroarenes, which first have to be reduced to carcinogenic aromatic diamines (anilines). Their reaction with highly poisonous phosgene results in bifunctional isocyanates, wherein large amounts of toxic hydrogen chloride accumulate as waste.

Therefore, great interest exists, on the part of the industry, for the development of synthesis methods which work without the use of phosgene and avoid the troublesome waste product hydrogen chloride. Furthermore, it is an advantage when nitroarenes do not have to be first reduced to aromatic amino compounds, but rather are suitable for being reacted directly into N-aryl carbamates and/or N-aryl isocyanates.

Thus, a method is already known from the U.S. Pat. No. 3,481,967 for the production of aromatic isocyanates, in which aromatic nitro compounds and carbon monoxide are suitable for being produced in the presence of transition metal catalysts. These transition metal catalysts comprise cobalt iodide and titanium tetrachloride. Technically feasible methods, however, require a high conversion and a selectivity of, if possible, at least 90% in order to be used successfully. Until now, these requirements could not have been fulfilled by methods of reductive carbonylation, which derive from aromatic nitro compounds.

Therefore, the industrial and scientific research has been concentrating predominantly on the development of methods in which the aromatic amino compounds initially produced from aromatic nitro compounds are reacted through oxidative carbonylation in the presence of carbon monoxide and one compound comprising organic hydroxyl groups into N-aryl carbamates and/or N-aryl isocyanates. For that purpose, it is necessary to add an oxidizing agent and to provide the presence of a catalyst, wherein, however, almost exclusively, expensive noble metal catalysts were suitable for being-used. One example of that is U.S. Pat. No. 5,194,660, which uses oxygen as the oxidizing agent and macrocyclic noble metal complex catalysts for the oxidative carbonylation of aromatic amines in the presence of carbon monoxide and of one compound comprising organic hydroxyl groups. Among the disadvantages of this method are the use of large amounts of lithium iodide as a promoter and the mixture of the reactive gases CO and $O_2$, which are technically not completely controllable within the explosive limits.

Thus, methods of reductive carbonylation have safety advantages compared to the oxidative carbonylation in the presence of hydrogen. All previously known methods for reductive carbonylation of nitro compounds, however, also have considerable disadvantages because they either do not derive from particularly inexpensive nitroarenes as the starting materials, in particular however, because they use expensive, and thus, compared to classical phosgenation methods, uneconomical, noble metal catalysts, which often do not even achieve conversion and selectivity values of over 90%. An overview of actual developments is offered by F. Paul, *Coordination Chemistry Reviews* 203 (2000) 269-323 and F. Ragaini et al. *Advanced Synthesis & Catalysis* 346 (2004) 63-71.

Therefore, the aim of developing a method for the production of N-aryl carbamates and/or N-aryl isocyanates, which, starting from aromatic nitro compounds through reductive carbonylation, is suitable for being used in high yields and with great selectivity, arises.

These multiple requirements can only be achieved through the use of specific catalysts, as they are the subject matter of this invention.

It has now been found that a method for producing N-aryl carbamates (urethanes) and/or N-aryl isocyanates through reductive carbonylation of aromatic nitro compounds in the presence of compounds carrying carbon monoxide and organic hydroxyl groups leads to excellent results, when the carbonylation is carried out in the presence of catalysts, which are anionic N,O chelate ligands of the general type $[M(N\sim O)^{1-}{}_2]$ or $[M(O\sim N\sim N\sim O)^{2-}]$ and contain a bivalent or trivalent transition metal of the groups 5 to 11. The method according to the present invention relies upon the Schiff base complex, known in the literature, wherein complexes of the inexpensive 3d metal cobalt exhibit particularly high activity. Complexes of the type cobalt-salen and cobalt-salophen (formulas A and B, see below) have proven themselves to be particularly suitable catalysts. Their common structure elements are two salicylidene amino groups, linked through a diamino spacer X. These catalysts have the following general lead structure (formula scheme I):

Salen-type, Formula A ($R^1$=H, Me, Ph)

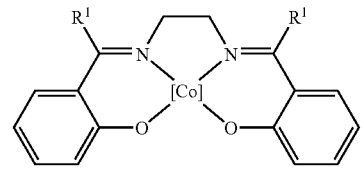

Salophen-type Formula B ($R^1$=H, Me, Ph)

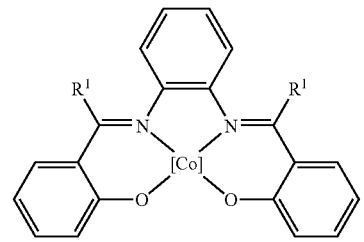

Formula scheme I

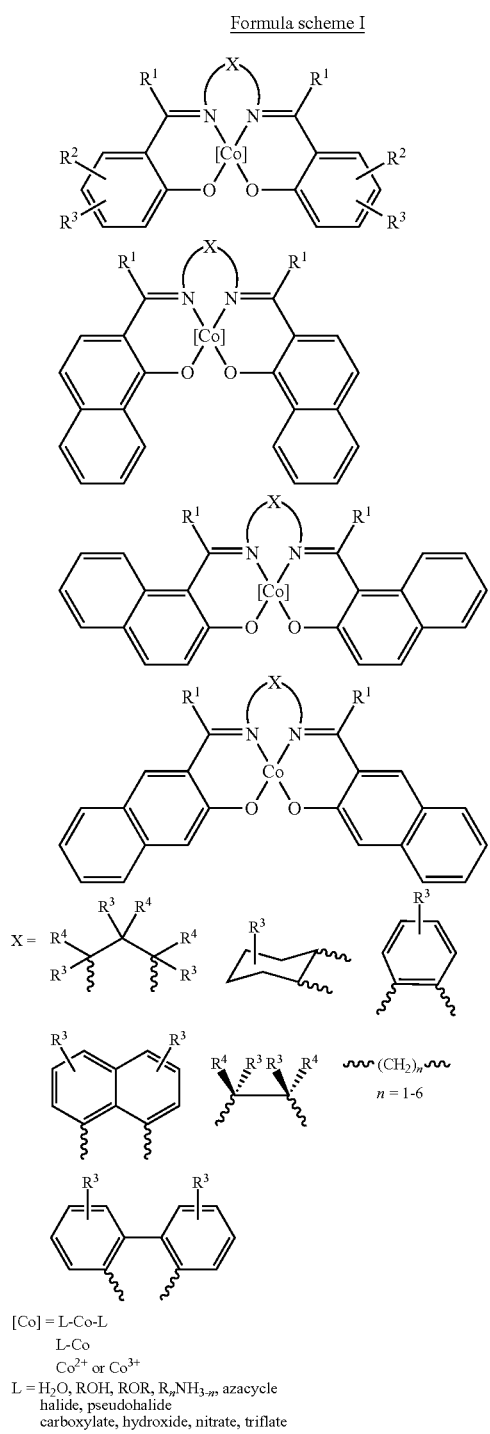

[Co] = L-Co-L
  L-Co
  Co²⁺ or Co³⁺
L = H₂O, ROH, ROR, R$_n$NH$_{3-n}$, azacycle
  halide, pseudohalide
  carboxylate, hydroxide, nitrate, triflate In these formulas,
$R^1$ represents hydrogen, an alkyl residue with 1 to 20 carbon atoms, an aryl- or heteroaryl group, an OR-group, in which R stands for hydrogen or an alkyl group with 1 to 20 carbon atoms, or mean NRR', in which R and R' mean hydrogen or respectively one aryl or alkyl group with 1 to 20 C atoms or are suitable for forming a ring system together with a nitrogen atom as a heteroatom;

$R^2$ represents hydrogen, an alkyl group with 1 to 20 carbon atoms, an aryl group or heteroaryl group, which is linked over one or two C—C bonds annellated with the salicylate building block, a keto group —COR or —COOR, —COOH, fluorine, chlorine, bromine, iodine, OH, OR or NRR', whereby R or R' are suitable for having the aforementioned meanings and $R^2$ is suitable for substituting the aromatic ring 1 to 4 times;

$R^3$ and/or $R^4$ are suitable for being hydrogen, an alkyl group with 1 to 20 carbon atoms, an aryl or heteroaryl group, a keto group, —COR, —COOR, —COOH, fluorine, chlorine, bromine, iodine, OH, OR or NRR', wherein R or R' are suitable for having the aforementioned meanings;

L represents H₂O, R$_n$NH$_{3-n}$, halide, sulfonate (e.g. triflate, tosylate), pseudohalide (e.g. CN, SCN, OCN, N₃), an azaarene, a cyclic or acyclic amine or ketimine R₂C=NR', an aliphatic ether or an aliphatic or aromatic alcohol. In this, R and R' represent an aryl or alkyl group with 1 to 20 C atoms, an —O-alkyl, NH(alkyl) or —N(alkyl)₂ group. Both the catalyst complexes with divalent cobalt and those with trivalent cobalt are catalytically active. This fact is represented by the [Co] formulation: if illustratively two neutral ligands L are coordinated additionally to the N₂O₂²⁻ ligand at cobalt [Co], then a neutral cobalt(II) complex or a cationic cobalt(III) complex with a non-coordinating anion is involved; if an anion L and neutral Ligand L' are coordinated at [Co], then a cobalt(III) neutral complex is involved. The ligands L may also be absent in the catalyst precursor isolated as the substance. In solution, L are usually solvent molecules; they are usually suitable for being substituted easily by the reacted substrates.

X=any alkylene or arylene building block, which links both imino nitrogen atoms with each other. This unit X is suitable for being linked via its central substituents $R^3$ or $R^4$ with further molecular, macromolecular or inorganic building elements as well.

Not only the highly active and selective salen and salophene type catalyst complexes are preferred, but also further catalysts with [M(O~N~N~O)₂₋] ligands shown in Table 1 (Cf. embodiments). Particularly preferable are the highly active catalyst complexes, which are listed in Table 1 (cf. embodiments). The assignment of the particularly preferred catalyst complexes to the structure formula is indicated in the following:

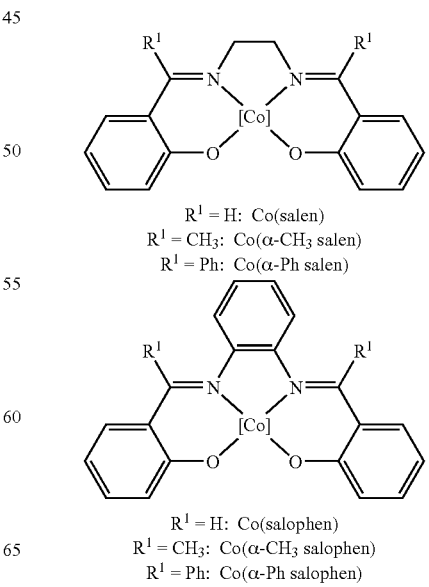

$R^1$ = H: Co(salen)
$R^1$ = CH₃: Co(α-CH₃ salen)
$R^1$ = Ph: Co(α-Ph salen)

$R^1$ = H: Co(salophen)
$R^1$ = CH₃: Co(α-CH₃ salophen)
$R^1$ = Ph: Co(α-Ph salophen)

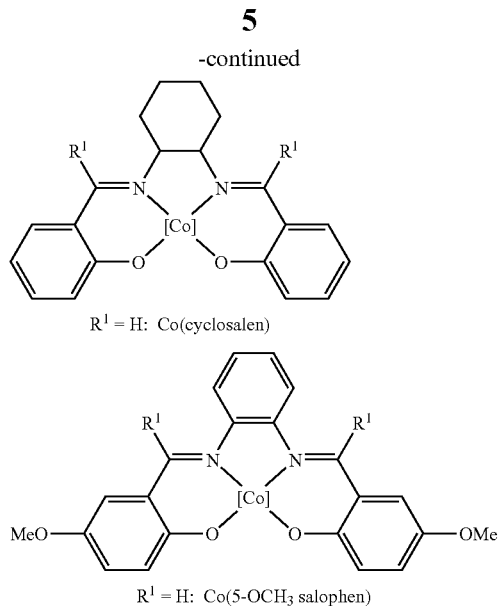

R¹ = H: Co(cyclosalen)

R¹ = H: Co(5-OCH₃ salophen)

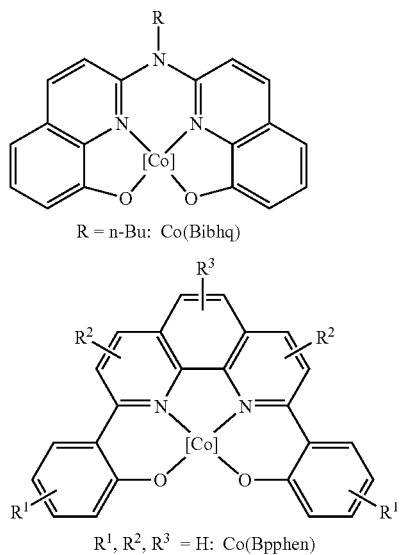

R = n-Bu: Co(Bibhq)

R¹, R², R³ = H: Co(Bpphen)

Catalysts according to the present invention are also metal complex compounds with other dianionic $N_2O_2$ chelate ligands, which unite carboxylate functions, azaarene functions, phenolate functions and/or metallated carboxylic acid amide functions within themselves. Suitable ligands with particularly preferable structure elements are described in more detail as cobalt complexes in the following formula scheme II and formula scheme III:

Formula scheme II

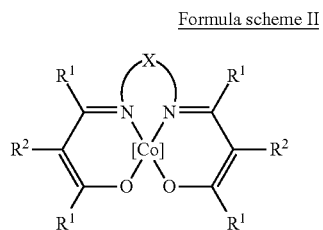

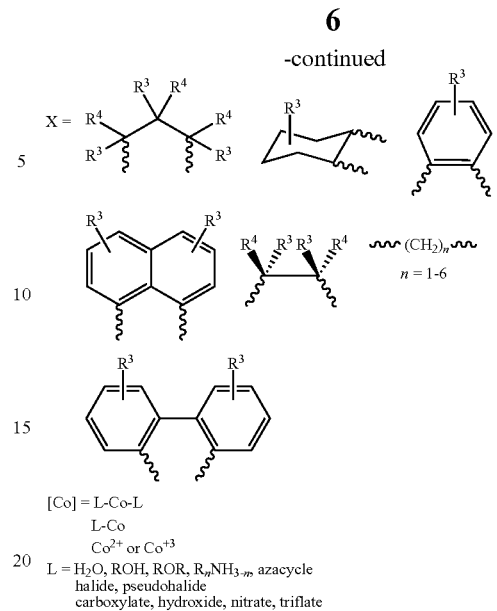

[Co] = L-Co-L
L-Co
Co²⁺ or Co⁺³
L = H₂O, ROH, ROR, R_nNH_{3-n}, azacycle
halide, pseudohalide
carboxylate, hydroxide, nitrate, triflate Formula scheme III

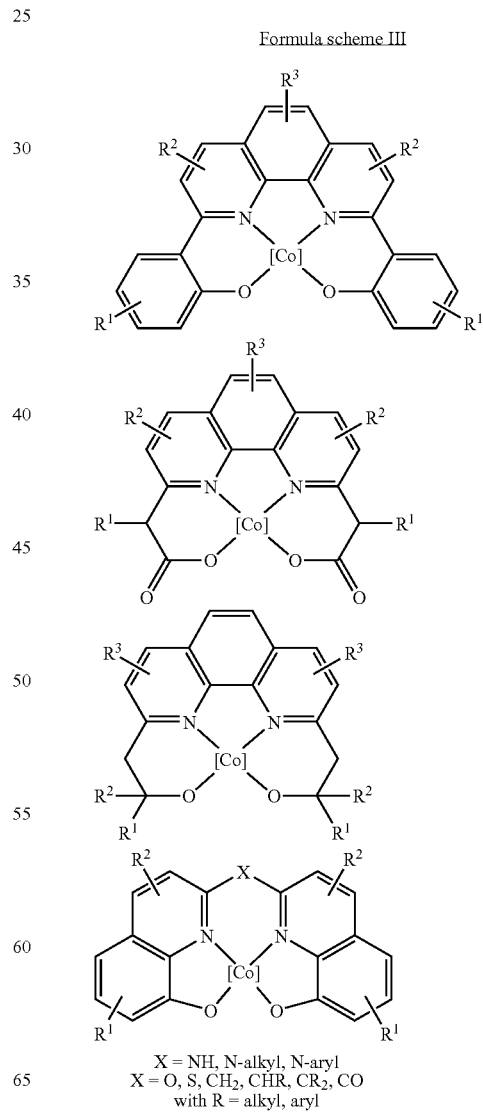

X = NH, N-alkyl, N-aryl
X = O, S, CH₂, CHR, CR₂, CO
with R = alkyl, aryl

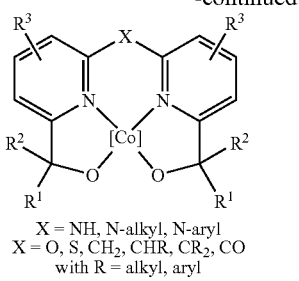
X = NH, N-alkyl, N-aryl
X = O, S, CH$_2$, CHR, CR$_2$, CO
with R = alkyl, aryl
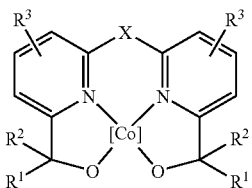
X = NH, N-alkyl, N-aryl
X = O, S, CH$_2$, CHR, CR$_2$, CO
with R = alkyl, aryl
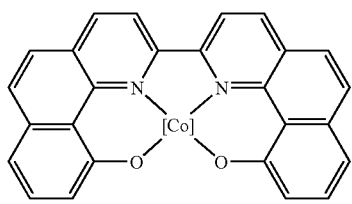
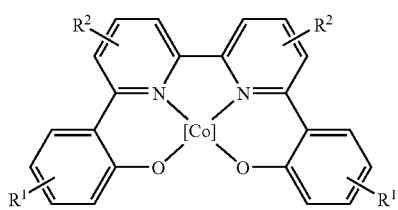
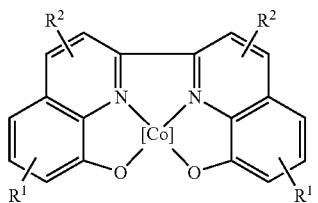
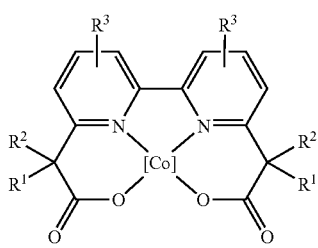
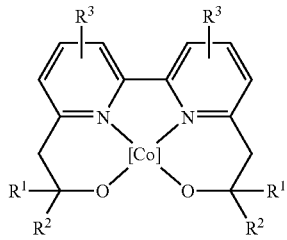
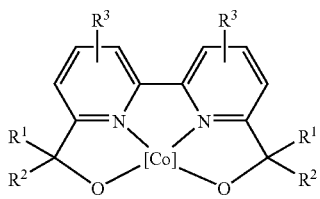
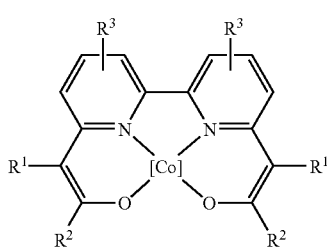
As alternative catalysts in place of a dianionic N$_2$O$_2$ ligand, two monoanionic, at least bidentate N,O chelate ligands can also be used (formula scheme IV).
Formula scheme IV
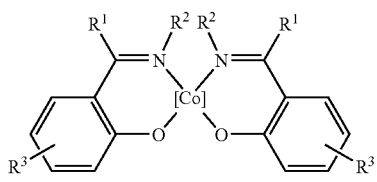
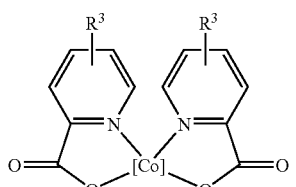
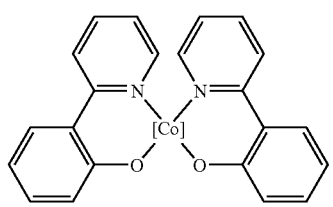
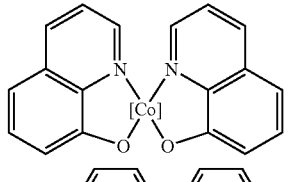
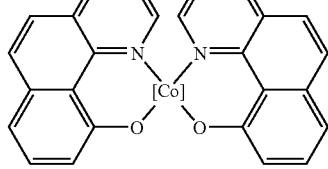

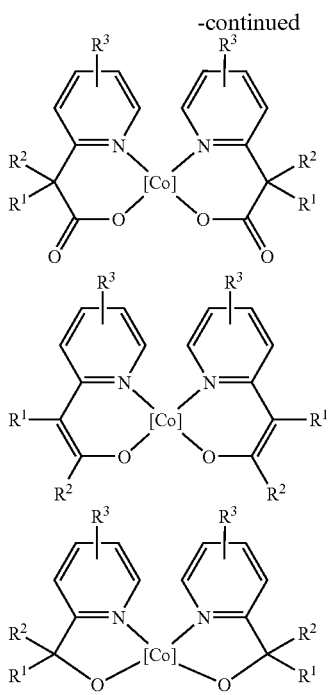

In formula schemes III and IV, the following applies for the substituents:

$R^1$ and/or $R^2$=hydrogen, an alkyl residue with 1 to 20 carbon atoms, an aryl group or heteroaryl group, an OR group, in which R stands for hydrogen, an aryl group or an alkyl group with 1 to 20 carbon atoms, or mean NRR', in which R and/or R' mean hydrogen, an aryl group or an alkyl group with 1 to 20 C atoms, respectively, or are suitable for forming a ring system together with a nitrogen atom as a hetero atom;

$R^3$=hydrogen, an alkyl group with 1 to 20 carbon atoms, an aryl group or heteroaryl group, which is linked over one or two C—C bonds annellated with the salicylate building block, a keto group —COR, COOR, COOH, fluorine, chlorine, bromine, iodine, OH, OR or NRR', which are suitable for having the aforementioned meanings, wherein $R^3$ is suitable for substituting the aromatic ring 1 to 4 times;

With these catalysts, conversions and selectivities of over 95% are able to be achieved, i.e. yields of over 90%, in relation to the nitroarenes used or in relation to a mixture of nitroarene and aniline.

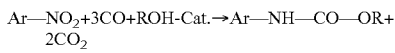

The reaction occurs in the same way with di- and polynitro compounds as well. As disclosed in embodiment 5, the TDI methylcarbamate also may be produced.

The method according to the present invention is suitable for being carried out with particularly good yields and proceeds when the aniline produced through reduction of the aromatic nitro compounds is used in amounts of up to 200 mol-%. Although the addition of one aniline is not required for the method according to the present invention (embodiment 4), considerably better yields are able to be achieved when the ratio of nitroarene to aniline is 100:10 mol-% (embodiments 1 and 2 and Table 2). The best yields were achieved with a ratio of nitroarene to aniline of 100:200 mol-% (embodiment 3). The following reaction equation describes this advantageous borderline case of the reacted substances of the method according to the present invention:

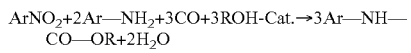

The reaction occurs in the same way with di- and polynitro compounds as well. In the variations in which the nitroarene is reductively carbonylated in the presence of 1-2 molar equivalents aniline, it has been proven to be advantageous to remove, to a certain extent, the water formed during the reaction from the reaction mixture through chemical or physical methods, since water may cause, under unfavorable conditions, the hydrolysis of the carbamate formed. Even without the removal of water, however, mostly selectivities greater than 90 percent are achieved. Traces of water, on the other hand, are advantageous, since water and CO are involved in the reduction of nitroarenes to aniline derivatives occurring as intermediates under certain conditions.

The complex compounds with cobalt as the central atom are particularly preferable. However, good results are also achieved with manganese, chromium, nickel, copper, as well as relatively few 4d metals, such as rhodium and ruthenium and 5d metals, such as osmium and platinum. The metal complex catalyst is applied in a concentration of 0.05 to 10 mol-%, preferably 0.1 to 3 mol %.

Preferably, the reaction is carried out in an autoclave at temperatures of 80 to 220° C. under a carbon monoxide pressure of 10 to 100 bar in the presence of an aliphatic or aromatic alcohol. Methanol, in particular, proved itself.

Particularly good results are achieved in the presence of an acid promoter. This is applied in different concentrations, preferably, however, in equimolar ratio relative to the catalyst complex (cf. Table 3 in the embodiments). The acid promoter is either a Lewis acid, such as $BF_3$ or the tosylate $B(OTs)_3$, which provides a protonic acid in combination with water or the OH-containing organic component of this method, or the acid promoter is itself a protonic acid. Particularly preferable are strong protonic acids with a pKs value of less than 5. For this purpose, p-toluenesulfonic acid, trifluoromethyl acid or nonafluoro-n-butylsulfonic acid, camphorsulfonic acid, particularly, but also polymeric acids carrying $SO_3H$ groups, for example acid ion exchange resin based on sulfonated polystyrenes, but also inorganic solid bodies as acids, such as acid aluminum silicates (zeolites) have proven themselves. Other acid promoters comprise aliphatic and aromatic, molecular and polymer-bound carboxylic acids, for example trifluoroacetic acid and higher homologs, p-chlorobenzoic acid, dicarboxylic acids, sulfuric acid derivatives, for example fluorosulfonic acid, phosphoric acid and its partially esterified aromatic and aliphatic derivatives, e.g. $(RO)_2PO(OH)$, aromatic and aliphatic phosphonic acids R—$PO(OH)_2$ and phosphinic acids $R_2PO(OH)$. Lastly, pure inorganic mineral acids, tetrafluoroboric acid and hexafluorophosphoric acid find use as promoters.

During the method according to the present invention, initially aniline derivatives and N-aryl carbamates (urethanes) might be formed as intermediates through the reductive carbonylation. From these intermediates, the alcohol is suitable for being cleaved off by thermal treatment in a simple way. Thus, the following particularly advantageous autocatalytic reaction sequence results, which is made possible through catalysts of the type described here in the presence of the acid promoters:

Di- and polynitro compounds are reacted in the same way. See embodiment 5.

The thermolytic cleavage of isolated carbamates to isocyanates and organic hydroxy compounds is a known technique. It is, however, also possible to carry out the reactions described here in such a way that aniline derivatives and N-aryl carbamates are only formed in traces and aryl isocyanates are formed directly under the reaction conditions preferably as the end product. For this purpose, the reactions are carried out either homogenously, preferably not in alcohols as the solvent, but rather in an inert solvent, for example chlorobenzene or toluene in the presence of small amounts of alcohol. A heterogeneous carrier of the catalyst complex and promoters on inorganic or organic carrier material, for example on acid aluminum oxide $Al_2O_3$, on silica gel, on sulfonated polystyrene, in aluminum silicate cage structures, such as zeolite Y, or mesoporous silica materials, such as MCM-41 or MCM-48, have proven themselves for this purpose as well (concerning the term MCM: Zhao et al, *Ind. Eng. Chem. Res.* 35 (1996) 2075).

Both mononitro compounds as well as dinitro compounds are suitable for being the starting material for the method according to the present invention. With the use of dinitro compounds, initially mono-, then di-N-aryl carbamates are formed, from which di-N-aryl isocyanates are suitable for being formed through thermolysis. It is, however, also possible to conduct the reaction in such a way that di-N-aryl isocyanates are formed directly.

The method according to the present invention is explained in more detail through the following examples:

EMBODIMENT 1

Reaction:

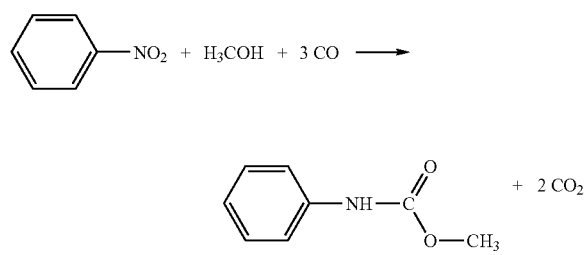

The aforementioned reaction was carried out in a 100 cm³ stainless steel autoclave with a polytetrafluoroethylene beaker as an insert. 0.196 g (0.5 mmol) N,N'-bis(salicylidene)-1,2-phenylene-diaminocobalt (II) monohydrate, 0.0870 g (0.5 mmol) p-tolylsulfonic acid as a promoter or cocatalyst, 0.0548 g (0.59 mmol) aniline, 0.6534 g (5.3 mmol) nitrobenzene and 4.172 g (13.05 mmol) methanol were mixed in the autoclave. The autoclave was flushed with nitrogen gas three times and then carbon monoxide gas was introduced at room temperature at a pressure of 50 bar.

After the autoclave's gas supply had been interrupted, the autoclave was inserted into an aluminum heating block, which had been heated to 200° C. Within 5 minutes the autoclave reached a reaction temperature of 170° C., which was then held continuously. After a reaction duration of 7 hours, the autoclave was cooled with cold water and ice, until it reached room temperature after about 5 minutes. The reaction mixture was then qualitatively and quantitatively examined through gas chromatography, wherein naphthaline served as an internal standard. The conversion of nitrobenzene was 100%, the yield of methyl-N-phenylcarbamate 99%.

EMBODIMENT 2

Reaction:

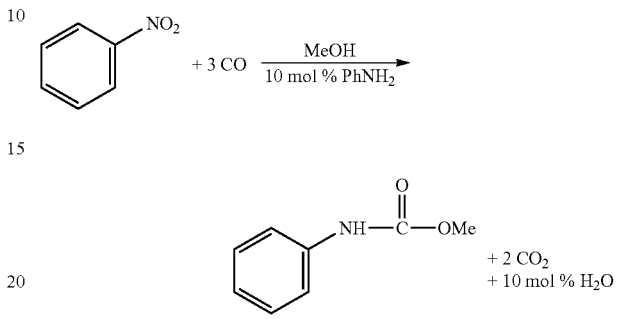

The reaction described in embodiment 1 was carried out again in a stainless steel autoclave with a polytetrafluoroethylene beaker of 100 cm³ capacity. 0.324 g (1.0 mmol) N,N'-bis(salicylidene)-ethylene-diaminocobalt (II), 0.172 g (=1.0 mmol) p-toluenesulfonic acid, 0.093 g (1.0 mmol) aniline, 1.251 g (10.2 mmol) nitrobenzene, 8.042 g (25.1 mmol) methanol were mixed in the autoclave. The autoclave was flushed three times with nitrogen gas and then carbon monoxide was introduced at room temperature at a pressure of 50 bar.

After the autoclave's gas supply had been interrupted, the autoclave was inserted into an aluminum heating block, which had been pre-heated to 200° C. After 5 minutes the autoclave reached a reaction temperature of 170° C., which was then held continuously. After a reaction duration of 7 hours, the autoclave was cooled with cold water and ice, until it reached room temperature after 5 minutes. The reaction mixture was then qualitatively and quantitatively examined through gas chromatography, wherein naphthaline served as an internal standard. The conversion of nitrobenzene was 100%, the yield of methyl-N-phenylcarbamate 99.0% and the selectivity of methyl-N-phenylcarbamate was likewise 99%.

EMBODIMENT 3

Reaction:

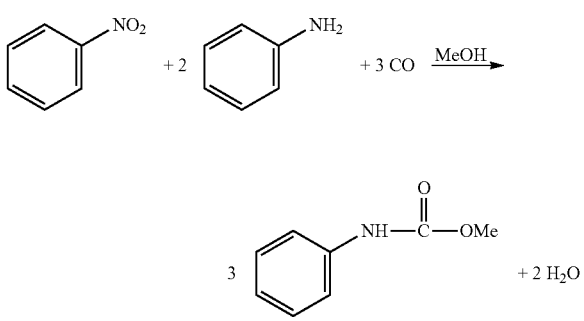

The aforementioned reaction was carried out in a stainless steel autoclave with a polytetrafluoroethylene beaker of 100 cm³ capacity as an insert. 0.0866 g (0.22 mmol) N,N'-bis (salicylidene)-1,2-phenylene-diaminocobalt(II) monohydrate, 0.0341 g (0.2 mmol) p-toluenesulfonic acid, 1.8650 g (20.05 mmol) aniline, 1.2354 g (10.0 mmol) nitrobenzene and 8.1370 g (254.3 mmol) methanol were mixed in the autoclave. The autoclave was then flushed five times with nitrogen gas and filled with carbon monoxide gas at room temperature at a pressure of 50 bar.

After interruption of the gas supply, the autoclave was inserted into an aluminum heating block, which had been pre-heated to 200° C. Within 5 minutes the autoclave reached a reaction temperature of 170° C., which was then held continuously. After a reaction duration of 7 hours, the autoclave was cooled with cold water and ice, until it reached room temperature after about 5 minutes. The reaction mixture was then qualitatively and quantitatively examined through gas chromatography, wherein naphthaline served as an internal standard. The conversion of nitrobenzene was 100%, the yield of methyl-N-phenylcarbamate 97.6%, while the selectivity of methyl-N-phenylcarbamate was likewise 97.6%.

TABLE 1

Examples of catalyst complexes used in the reductive carbonylation

| Item | Catalyst | Conversion of $PhNO_2 + PhNH_2$ [%] | $PhNHCOOCH_3$ Conversion (relative to $PhNO_2 + PhNH_2$) [%] | $PhNHCOOCH_3$ Selectivity (relative to $PhNO_2 + PhNH_2$) [%] |
|---|---|---|---|---|
| 1 | [$Co^{II}$salophen-$H_2O$] | 49.7 | 51.7 | 100 |
| 2 | [$Co^{II}$salophen-$H_2O$] | 42.1 | 46.9 | 100 |
| 3 | [$Co^{II}$salen] | 33.6 | 30.7 | 91.4 |
| 4 | [$Co^{II}$-α-$CH_3$-salen] | 61.5 | 51.2 | 83.3 |
| 5 | [$Co^{II}$-α-Ph-salen] | 54.0 | 42.7 | 79.1 |
| 6 | [$Co^{II}$cyclosalen] | 46.0 | 42.5 | 92.4 |
| 7 | [$Co^{II}$5-$OCH_3$-salophen] | 39.4 | 31.4 | 79.7 |
| 8 | [$Co^{II}$Bpphen][a] | 100 | 66.0 | 66.0 |
| 9 | [$Co^{II}$Bibhq]a | 78.0 | 66.0 | 84.0 |

[a] $n_{Cat}/n_{PhNO2}$ = 1/50
unitary conditions, the only variable is the catalyst
$n_{Cat}/n_{PhNO2}$ = 1/200
$n_{Cat}/n_{Promoter}$ = 1/1
$n_{PhNH2}/n_{PhNO2}$ = 2/1
$n_{MeOH}/n_{PhNO2}$ = 25/1
Promoter = p-TsOH
Temperature = 170° C.
Reaction duration = 7 h
CO pressure = 50 bar
The realization is carried out, apart from the amounts weighed out, as described in the patent embodiment 1.

TABLE 2

Effect of added aniline on the reductive carbonylation

| Item | $N_{PhNH2}/n_{PhNO2}$ | Conversion of $PhNO_2 + PhNH_2$ [%] | $PhNHCOOCH_3$ Conversion (relative to $PhNO_2 + PhNH_2$) [%] | $PhNHCOOCH_3$ Selectivity (relative to $PhNO_2 + PhNH_2$) [%] |
|---|---|---|---|---|
| 1 | 0 | 5.0 | 1.8 | 36.0 |
| 2 | 0.5 | 32.8 | 33.3 | 100 |
| 3 | 1 | 49.3 | 49.0 | 99.4 |
| 4 | 1.5 | 56.6 | 47.9 | 84.6 |
| 5 | 2 | 54.4 | 51.5 | 94.7 |
| 6 | 3 | 57.5 | 51.9 | 90.3 |
| 7 | 5 | 42.7 | 33.6 | 78.7 |

Unitary reaction conditions, the only variable is the ratio of aniline to nitro-benzene
Catalyst: [$Co^{II}$salophen]
$n_{Cat}/n_{PhNO2}$ = 1/200
$n_{Cat}/n_{Promoter}$ = 1/1
$n_{MeOH}/n_{PhNO2}$ = 25/1
Promoter = p-TsOH
Temperature = 170° C.
Reaction duration = 7 h
CO pressure = 50 bar

TABLE 3

Examples of acid promoters used in the reductive carbonylation

| Item | Promoter | Conversion of $PhNO_2 + PhNH_2$ [%] | $PhNHCOOCH_3$ Conversion (relative to $PhNO_2 + PhNH_2$) [%] | $PhNHCOOCH_3$ Selectivity (relative to $PhNO_2 + PhNH_2$) [%] |
|---|---|---|---|---|
| 1 | without promoter | 15.5 | 8.7 | 56.1 |
| 2 | p-$CH_3$—$C_6H_5$—$SO_3H$ | 47.5 | 46.9 | 98.7 |
| 3 | $C_4F_9SO_3H$ | 77.3 | 74.1 | 95.9 |
| 4 | $CF_3COOH$ | 56.3 | 51.2 | 90.9 |
| 5 | $CF_3SO_3H$ | 81.6 | 80.1 | 98.2 |
| 6 | Amberlite IR-120 (humid) 1:1 | 30.8 | 21.8 | 70.8 |
| 7 | Amberlite IR-120 (anhydrous) 1:1 | 25.6 | 23.1 | 90.2 |

Unitary reaction conditions, promoter in equimolar ratio to catalyst as only variable
Catalyst: [$Co^{II}$salophen]
$n_{Cat}/n_{PhNO2} = 1/200$
$n_{Cat}/n_{Promoter} = 1/1$
$n_{PhNH2}/n_{PhNO2} = 2/1$
$n_{MeOH}/n_{PhNO2} = 25/1$
Temperature = 170° C.
Reaction duration = 7 h
CO pressure = 50 bar

EMBODIMENT 4

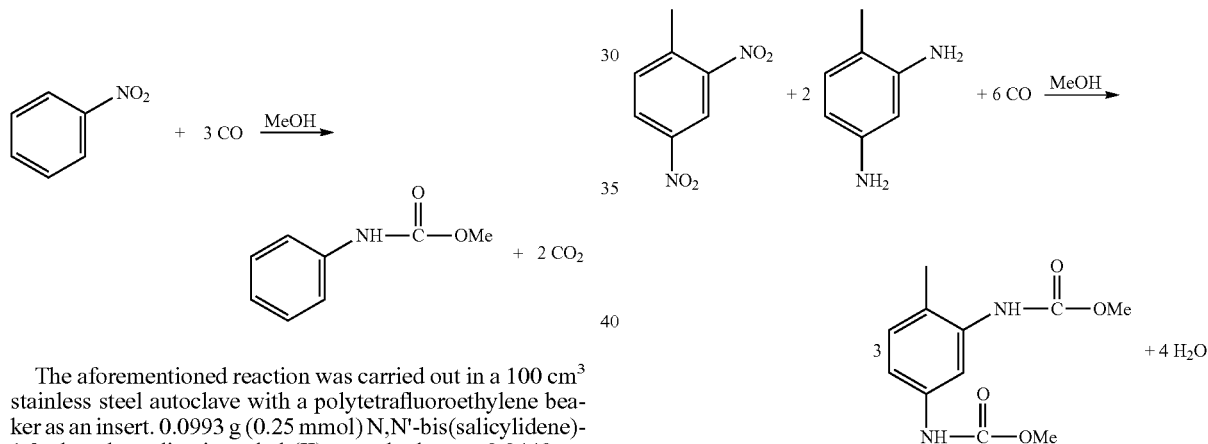

The aforementioned reaction was carried out in a 100 cm³ stainless steel autoclave with a polytetrafluoroethylene beaker as an insert. 0.0993 g (0.25 mmol) N,N'-bis(salicylidene)-1,2-phenylene-diaminocobalt(II)-monohydrate, 0.0440 g (0.26 mmol) p-toluenesulfonic acid, 0.6340 g (5.15 mmol) nitrobenzene, 4.3840 g (13.7 mmol) methanol were mixed in the autoclave. No aniline was added. The autoclave was flushed five times with nitrogen and then carbon monoxide gas was introduced at room temperature at a pressure of 50 bar.

After the autoclave's gas supply had been interrupted, the autoclave was inserted into an aluminum heating block, which had been pre-heated to 200° C. Within 5 minutes the autoclave reached a reaction temperature of 170° C., which was then held continuously. After a reaction duration of 7 hours, the autoclave was cooled with cold water and ice, until it reached room temperature after 5 minutes. The reaction mixture was then qualitatively and quantitatively examined through gas chromatography, wherein naphthaline served as an internal standard. The conversion of nitrobenzene was 48.3%, the yield of methyl-N-phenylcarbamate 41.8% and the selectivity of methyl-N-phenylcarbamate was 86.5%.

EMBODIMENT 5

Procedure to isolate the bis(methylcarbamate) of toluene-2,4-diisocyanate (TDI).

The reaction was carried out in a high-grade stainless steel autoclave fitted with a polytetrafluoroethylene beaker of 100 cm³ capacity. 0.01869 g (0.05 mmole) of N,N'-bis(salicylidene)-1,2-phenylidenediaminocobalt(II), 0.0086 g (0.05 mmole) of p-toluenesulfonic acid, 0.6103 (5.0 mmole) of 2,4-diaminoaniline, 0.4550 g (2.5 mmole) of 2,4-dinitrotoluene, 5.07 g (15.8 mmole) of methanol, where mixed in the autoclave. The autoclave was flushed three times with gaseous nitrogen, whereupon it was pressurized with 50 bar carbon monoxide. After interrupting the gas supply, the autoclave was inserted into an aluminum heating block that had been preheated to 200° C. The autoclave after five minutes reached a reaction temperature of 170° C. which then was kept constant. After a reaction time of 6 hours, the autoclave was cooled within 5 minutes to room temperature using water and ice. The reaction mixture was filtered and the solid substance so obtained was washed three times with cold methanol. Then the solid substance was dried in high vacuum for 5 h. Characterization was implemented by ¹H-NMR, MS, CHN analysis and melting point. 1.6520 g of TDI-methylcarbamate was isolated, indicating a yield of 92,6%.

EMBODIMENT 6

Procedure for urea isolation offering shorter reaction times and higher aniline proportions:

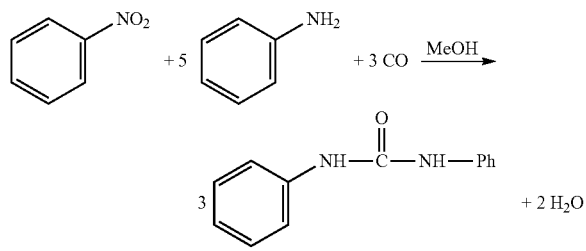

The above reaction was carried out in a high-grade stainless steel autoclave fitted with a polytetrafluoroethylene beaker of 100 cm$^3$ capacity. 0.0373 g (0.1 mmole) of N,N'-bis(salicylidene)-1,2-phenylenediaminocobalt(II), 0.0172 g (0.1 mmole( of p-toluenesulfonic acid, 4.6498 g (50.0 mmole) aniline, 1.2318 g (10.0 mmole) of nitrobenzene and 8.69 g (10 mmole) of toluene were mixed in the autoclave. The autoclave was flushed three times with gaseous nitrogen and then was pressurized with 50 bar carbon monoxide. After the gas supply was interrupted, the autoclave was inserted into an aluminum block that had been preheated to 200° C. Following 5 minutes, the autoclave reaction temperature reached 170° C. which thereupon was kept constant. Following 6 h of reaction, the autoclave was cooled with cold water and ice and reached room temperature in 5 minutes. The reaction mixture was filtered off and the solid substance so obtained was washed with toluene (3×10 ml). Thereupon the solid substance was dried in high vacuum for 4 h. Characterization was implemented by $^1$H-NMR, MS, CHN analysis and melting point. This test, not yet optimized, gave 3.0414 g of N,N'-diphenylurea, relating to a yield of 23.9%.

The invention claimed is:
1. A method for producing N-aryl carbamates (urethanes) and/or N-aryl isocyanates through reductive carbonylation of aromatic nitro compounds in the presence of carbon monoxide and organic compounds carrying hydroxyl groups, wherein the carbonylation is carried out
   in the presence of cobalt complex catalysts, which are anionic N,O-chelate ligands of the general type $[M(N{\sim}O)^{1-}{}_2]$ or $(M(O{\sim}N{\sim}N{\sim}O)^{2-}]$ and
   in the presence of up to 2 mol equivalents of an aromatic amine calculated on the used aromatic nitro compound.
2. The method defined in claim 1 wherein the cobalt complex catalyst is used in a concentration of 0.1-10 mol %.
3. The method defined in claim 1 wherein the reaction is carried out in an autoclave at temperatures of about 80-260° C. under a carbon monoxide pressure of about 10-100 bar in an aliphatic or aromatic alcohol.
4. The method defined in claim 3 wherein the reaction is carried out in methanol.
5. The method defined in claim 1 wherein the reaction is carried out in the presence of an acid promoter with a pK$_S$-value under 5.
6. The method defined in claim 1 wherein the reaction is carried out in the presence of p-toluenesulfonic acid or a polymeric acid carrying SO$_3$H groups.
7. The method defined in claim 1 wherein the N-aryl isocyanates are formed by cleaving off alcohol from the N-aryl carbamates (urethanes) initially formed.
8. The method defined in claim 1 wherein the reaction leads directly to N-aryl isocyanates in a single-step method and the reaction is performed homogenously in an inert solvent in the presence of small amounts of an alcohol or heterogeneously with catalyst complexes and promoters on inorganic or organic supports.
9. The method defined in claim 1 wherein aromatic dinitro compounds are converted into the corresponding di-N-aryl carbamates and/or di-N-aryl isocyanates.

* * * * *